United States Patent [19]

Bourgault

[11] Patent Number: 5,601,890
[45] Date of Patent: Feb. 11, 1997

[54] IRRADIATION CROSSLINKED ACRYLATED POLYOLEFIN TUBING

[75] Inventor: Clement U. Bourgault, Fitchburg, Mass.

[73] Assignee: Alpha Wire Corporation, Elizabeth, N.J.

[21] Appl. No.: 332,639

[22] Filed: Nov. 1, 1994

Related U.S. Application Data

[63] Continuation of Ser. No. 59,233, May 7, 1993, abandoned.

[51] Int. Cl.$^6$ ...................................................... B29D 22/00
[52] U.S. Cl. ...................... 428/35.1; 428/34.9; 428/36.9; 428/36.92
[58] Field of Search .................... 428/34.9, 35.1, 428/35.7, 36.9, 36.91, 36.92, 520, 522

[56] References Cited

U.S. PATENT DOCUMENTS 5,158,815 10/1992 Doheny, Jr. et al. .................. 428/34.9
5,212,001 5/1993 Brant et al. ............................ 428/34.9

OTHER PUBLICATIONS

R. Kraus et al., "Adv. in Heat–Shrink Tech", *IEEE Elec. Insulation Magazine*, 4:31–34 (May/Jun. 1988).
J. Hoffman, "Insulation Enhancement with Heat–Shrinkable Comp.," *IEEE Elec. Insulation Mag.*, 7:33–38 (Mar./Apr. 1991).

*Primary Examiner*—James J. Seidleck
*Assistant Examiner*—Michael A. Williamson
*Attorney, Agent, or Firm*—Wolf, Greenfield & Sacks, P.C.

[57] ABSTRACT

The present invention provides an acrylated polyolefin tubing (12) crosslinked by irradiation. The tubing (12) is electrically insulating and can be heat shrunk upon a substrate (14) for perfecting a fluid tight seal therewith. The tubing (12) remains adhesively sealed to the substrate (14) and maintains heat sealability after cyclic autoclave sterilization. Moreover, the subject tubing does not permanently discolor after cyclic gamma or electron beam sterilization. The tubing (12) is particularly useful as an outer sheath for electro-surgical instruments (18).

6 Claims, 1 Drawing Sheet

IRRADIATION CROSSLINKED ACRYLATED POLYOLEFIN TUBING

This is a continuation of application Ser. No. 08/059,233 filed on May 7, 1993, now abandoned.

TECHNICAL FIELD

The present invention relates to a acrylated polyolefin tubing crosslinked by irradiation. More specifically, the present invention provides a tubing which remains both adhesively sealed to a substrate and maintains heat sealability with itself after cyclic autoclave sterilization and does not permanently discolor after cyclic gamma or electron beam sterilization.

BACKGROUND OF THE INVENTION

Due to advances in polymer science, the number of applications for polymeric tubing have drastically increased. These advances have resulted in polymeric tubing having outstanding thermal, mechanical, and insulative properties. Moreover, due to the wide variety of base resins, additives, and processing techniques currently available, tubing can be designed having specific physical properties, e.g. flexibility, flame resistant, chemical resistant, etc.

Typically, the base resins used for such polymeric tubing include polyolefins, polyvinylchloride (PVC), fluoropolymers, elastomers, and blends thereof.

Depending upon the materials and processing techniques used, such tubing may be "heat-shrinkable". For example, polyolefin materials are commonly extruded, irradiation crosslinked, and then expanded to form heat shrinkable tubing, as is common in the art and as described in: R. Kraus and D. Ryan, "Advances in Heat-Shrink Technology," IEEE Electrical Insulation Magazine (1988) Vol.4, 31–34; and J. W. Hoffman, "Insulation Enhancement with Heat-Shrinkable Components," IEEE Electrical Insulation Magazine (1991) Vol.7, 33–38. Upon subsequent application of heat, such tubing shrinks to approximately its originally extruded size and shape.

Although heat shrinkable polyolefin tubing exhibits many desirable mechanical, thermal, and insulative properties, in many applications including those having repeated exposure to high temperature and/or pressure, such polyolefin materials fail to maintain an adhesive bond to a substrate and/or fail to maintain heat sealability (ability to remain bonded to itself). Consequently, in these applications, an inner sealant or adhesive mastic liner is commonly used to help maintain a fluid tight seal. For example, U.S. Pat. No. 3,297,819 to Wetmore; R. Kraus and D. Ryan, "Advances in Heat-Shrink Technology," *IEEE Electrical Insulation Magazine* (1988) Vol.4, 31–34; and J. W. Hoffman, "Insulation Enhancement with Heat-Shrinkable Components," *IEEE Electrical Insulation Magazine* (1991) Vol.7, 33–38 all describe a heat shrinkable tubing including an inner thermoplastic or mastic liner which maintains an adhesive bond with an inner substrate, and an outer heat shrinkable liner which is typically crosslinked. Such tubing may be co-extruded thereby providing a tubing having the inner non-crosslinked liner and the outer crosslinked liner.

Many problems are associated with such tubing, particularly when used in environments having cyclic exposure to high temperatures and pressures. For example, when such tubing is used in the medical or food industries where cyclic autoclave sterilization is common, the inner liner of the tubing melts and flows in response to the sterilization temperatures and pressures. Moreover, at sterilization temperatures, the outer liner tends to undergo additional shrink thereby causing the melted inner liner to ooze or flow from the tubing. The melt and flow of the inner liner, although acceptable in some applications, is not acceptable in most medical applications. For example, one particular medical applications includes the use of the heat shrinkable tubing in connection with electro-surgical laparoscopic instruments. Such instruments typically include a cylindrical electrically conducting member having one of many possible surgical attachments secured to one end for performing a variety of surgical procedures, i.e. providing suction, irrigation, coagulating vessels, etc. The opposite end of the conducting member is securable to a hand-held control module which allows a surgeon to control the surgical attachment.

The conducting member includes a sheath or tubing disposed circumferencally about its length for electrically insulating the conducting member. The tubing is preferably transparent and of the heat shrink variety so that it may be easily applied about the conducting member. Moreover, the tubing must maintain an adhesive seal with the conducting member and maintain heat sealability with itself after cyclic autoclave sterilization in order to prevent the ingress of moisture between the conducting member and the tubing. The tubing must maintain its electrical insulating properties along with a sufficient hot modulus. Furthermore, the tubing must maintain all of these aforementioned properties after cyclic gamma, electron beam, or ethylene oxide gas sterilization procedures. Finally, the tubing must maintain its thermal stability at sterilization temperatures and not flow in response to sterilization heat and pressure.

Prior art heat shrink polyolefin tubing, including those made from KYRAN™ (a registered trademark of Penwalt Co. for its vinylidene fluoride resin) and crosslinked polyolefins such as those disclosed in U.S. Pat. Nos. 3,592,881 to Ostapchenko, 3,990,479 to Stine et al., and 3,852,177 to Atchison et al., may provide the necessary hot modulus strength, but lose their adhesive sealability to a substrate and lost sealability after exposure to the high temperatures and pressures associated with autoclave sterilization. Moisture leaks into the interface between the conducting member and the tubing, thus causing potential electrical and sterilization problems. Such prior art tubing also permanently discolor after cyclic gamma sterilization. Furthermore, the prior art tubing lose their electrical insulating properties after cyclic sterilization. Although co-extruded tubing such as that shown in U.S. Pat. No. 3,297,819 to Wetmore, may maintain a seal after repetitive autoclave sterilizations, the temperature and pressure associated with sterilization cause the inner liner of adhesive material to flow out of the tubing rendering the instrument unusable and susceptible to leaks.

Thus, a tubing is needed which is thermally stable and will not flow at sterilizations temperatures while simultaneously providing sufficient hot modulus, electrical insulative properties, permanent transparency, heat sealability, and adhesiveness after cyclic autoclave, gamma, and electron beam sterilization.

SUMMARY OF THE INVENTION

In accordance with the present invention, there is provided a tubing consisting essentially of a crosslinked acrylated polyolefin being adhesive to a substrate and heat sealable after cyclic autoclave sterilization and being resistant to permanent dis-colorization after cyclic gamma and electron beam sterilization.

BRIEF DESCRIPTION OF THE DRAWINGS

These advantages of the present invention will be readily appreciated as the same becomes better understood by reference to the following detailed description when considered in connection with the accompanying drawings wherein.

DETAILED DESCRIPTION OF THE INVENTION

Figure 1:
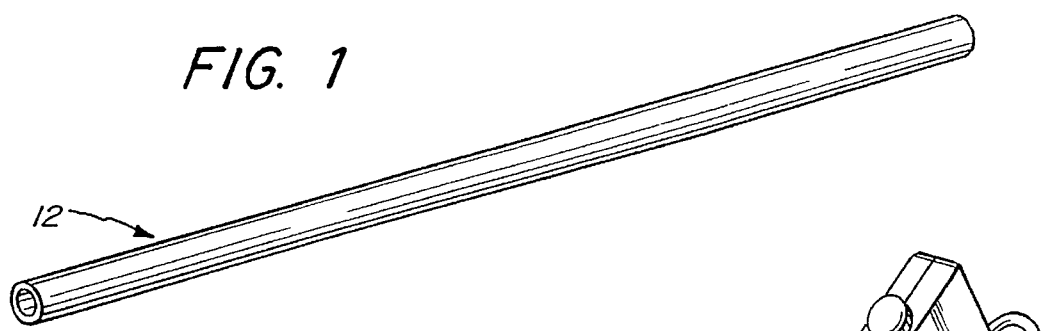
FIG. 1 is a perspective view showing the subject polymeric tubing.

The present invention is a polymeric tubing consisting essentially of a crosslinked acrylated polyolefin. The subject tubing is particularly well suited for use as an outer sheath on substrates, e.g. food preparation equipment, surgical instruments, etc., which are exposed to cyclic autoclave, gamma, or electron beam sterilization, as will be described. By cyclical, it is meant that the instruments are exposed to repeated sterilization procedures during their useful life, as opposed to being disposable.

The subject tubing is an acrylated polyolefin, preferably NUCREL™ 403 sold by Dupont. NUCREL™ is a branched, random ethylene methacrylic acid copolymer with carboxyl groups distributed along the chain. However, other acrylated polyolefins made from ethylene-methacrylic acid may be used. The resulting resin should have a melt index range from 1.5 to 500 and an acid number from 4 to 90.

Additives may be added to the resin in the form of extrusion aids, anti-block, and anti-slip agents but "neat" resins (no additives) are preferred for the purposes described herein. The resin is extruded into a tube form in a manner similar to standard tube/pipe/profile extrusion processes and is consistent with the current state-of-the-art practice.

The acrylated polyolefin is crosslinked in order to increase the polymer's hot modulus. The crosslinking is preferably performed by irradiating the tubing. For example, a typical 3/16 inch tube can be effectively crosslinked by means of an electron beam 500 KV accelerator with 96 passes at a current of 5.3 MA, and a linear speed of 295 FPM for a target hot modulus of 100 psi. These techniques are consistent with those used by practitioners versed in the current state of the art. The specific machine used to accomplish this was a resonant high voltage cup core accelerator tuned to operate at 9.9 KC.

Crosslinking by irradiation improves the hot strength of the polymer and imparts a memory allowing the polymer to be fashioned into a heat shrink. For example, once the tubing has been crosslinked, the tubing can be expanded. Subsequently, when the tubing is heated, the expanded tubing shrinks to return to its pre-expanded shape. U.S. Pat. No. 2,981,663 (1961) issued to Electronized Chemicals Corporation is an early patent describing the crosslinking processes. The '663 patent is representative of the current technical definition of crosslinking of crystalline polymers like polyethylene and is incorporated herein by reference.

Although polyolefins other than those made from ethylene-methacrylic acid may be used, those made from ethylene-methacrylic acid are preferred for a number of reasons. One advantage of using the acrylated polyolefin of the subject invention as compared to an additive acrylated crosslinking promoter such as described in U.S. Pat. No. 3,852,177 to Atchison et al., is illustrated in the following example.

A typical 3/16 inch tube made from an olefinic composition containing an acrylated crosslinking promoter was crosslinked by means of an electron beam 500 KV accelerator with 96 passes at a current of 11 MA, and a linear speed of 295 FPM for a target hot modulus of 100 psi. These techniques are consistent with those used by practitioners versed in the current state of the art. The specific machine used to accomplish this was a resonant high voltage cup core accelerator tuned to operate at 9.9 KC.

Under identical conditions, the subject acrylated polyolefin of the present invention required less than ½ of the beam current to achieve an equivalent modulus (consequently resulting in a lower dose). Additionally the subject acrylated polyolefin tubing does not require a blending or compounding operations to incorporate the acrylate into the polyolefin. Furthermore, any propensity towards leaching or exuding of the acrylate is eliminated as it is bound into the backbone of the molecule.

The subject polymeric tubing is heat shrinkable; that is, the tubing may be shrunk by the application of heat to form-fit about an object. As previously noted, heat shrinkable, crosslinked polyolefin films are known, as shown in U.S. Pat. No. 3,592,881 to Ostapchenko, and often find application is the packaging art. However, crosslinking such prior art films as tends to cause a loss of heat sealability and adhesiveness, particularly when used as tubing.

Unlike prior art crosslinked polyolefins, the subject tubing may be exposed to cyclic autoclave sterilization without losing its ability to maintain a fluid tight adhesive seal. In other words, the subject tubing remains adhesively sealed to a substrate, such as metal, glass, and plastic, and itself (heat sealability) even after repeated exposure to elevated temperatures and pressures. Prior art crosslinked tubing lose their heat sealability and ability to remain adhesively sealed to a substrate after cyclic autoclave sterilization. Consequently, the prior art tubing permits moisture to leak into the interface between the tubing and substrate, causing corrosion, insulating failure, and other associated problems.

Unlike other crosslinked polyolefins tubing, the subject tubing does not permanently discolor after cyclic exposure to gamma or electron beam sterilization. Any color change in the subject tubing is temporary and resorts back to the original polymer color within 24 hours or upon the application of heat. Surgical instruments are commonly exposed to such sterilization and in many applications, it is necessary for the tubing to remain transparent after sterilization.

With reference to FIG. 1, the subject tubing is generally shown at 12. The resin is extruded into a tube form. The extrusion process is similar to standard tube/pipe profile extrusion processes and is consistent with the current state-of-the-art practice. Sizes and wall thickness can vary in a wide range and are dependent on the application requirements as typical example sizes may vary from 0.101 inch to 4.00 inch inner diameter and wall thicknesses from 0.005 inch to 0.100 inch. These ranges are not to be construed as limitations on the product but typical representations of what may be required by applications encountered in the practice. The subject tubing 12 can subsequently be expanded and then disposed over a substrate and heat shrunk into a fluid tight adhesive seal therewith.

Alternatively, the tubing may not be expanded, thus producing a non-heat shrink tubing. Such tubing has been found to be an excellent material in the construction of catheters. In the past, catheters have often been made from polyvinylchloride (PVC). However, the PVC material discolors when exposed to gamma ray sterilization, even when color additives are used therewith. Moreover, PVC materials require special dispose procedures due to their hazardous nature.

Figure 2:
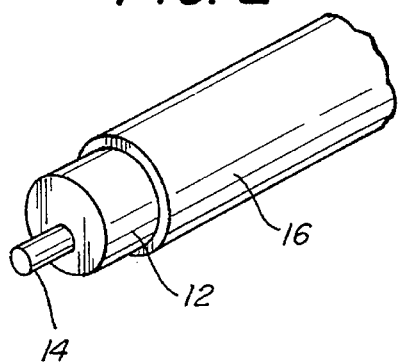
FIG. 2 is a perspective view of an cylindrically shaped substrate including the subject tubing disposed thereon along with a second outer tubing also disposed thereabout.

With reference to FIG. 2, a cylindrically shaped substrate is shown at 14. The substrate may be electrically conducting. Also, the substrate 14 may be comprised of such materials as glass, metal, plastic, etc. For example, the substrate 14 may comprise a glass electrode, such as those used to monitor the pH, or may comprise a metal conducting member. The substrate 14 includes the subject tubing 12 disposed circumferencally about its length. The tubing 12 is formed so as to have a inner diameter larger than the outer diameter of the substrate 14 thereby permitting the tubing 12 to be disposed over the substrate 14. The tubing 12 is subsequently heat shrunk into a fluid tight adhesive seal about the substrate 14. This fluid tight seal holds up after cyclic autoclave, gamma, electron beam, and ethylene oxide gas sterilization. Not only does the tubing 12 provide a fluid tight seal, it simultaneously maintains a sufficient hot modulus, heat sealability and electric insulative properties after cyclic sterilization.

Due to the adhesive nature of the polymeric tubing 12, a second tubing 16 may be disposed about the polymeric tubing 12, as shown in FIG. 2. The second tubing 16 may be an organic polymeric material and is preferable of the heat shrinkable variety thereby allowing the second tubing 16 to be easily applied to the polymeric tubing 12. In practice, the subject polymeric tubing 12 is heat shrunk upon the substrate 14, and thereafter the second tubing 16 is heat shrunk upon the polymeric tubing 12. Preferably, the second tubing 16 consists essentially of KYRAN™.

The polymeric tubing 12 adhesively bonds the second tubing 16 to the substrate 14. Thus, tubing which possesses generally desirable characteristics but which do not maintain a fluid tight seal with the substrate 14 after cyclic autoclave sterilization, can now be bonded or secured to the substrate 14 by utilizing the subject tubing 12 as an intermediate layer between the substrate 14 and the second tubing 16. The second tubing 16 remains adhesively sealed to the substrate 14 by the polymeric tubing 12, even after cyclic autoclave sterilization.

Figure 3:
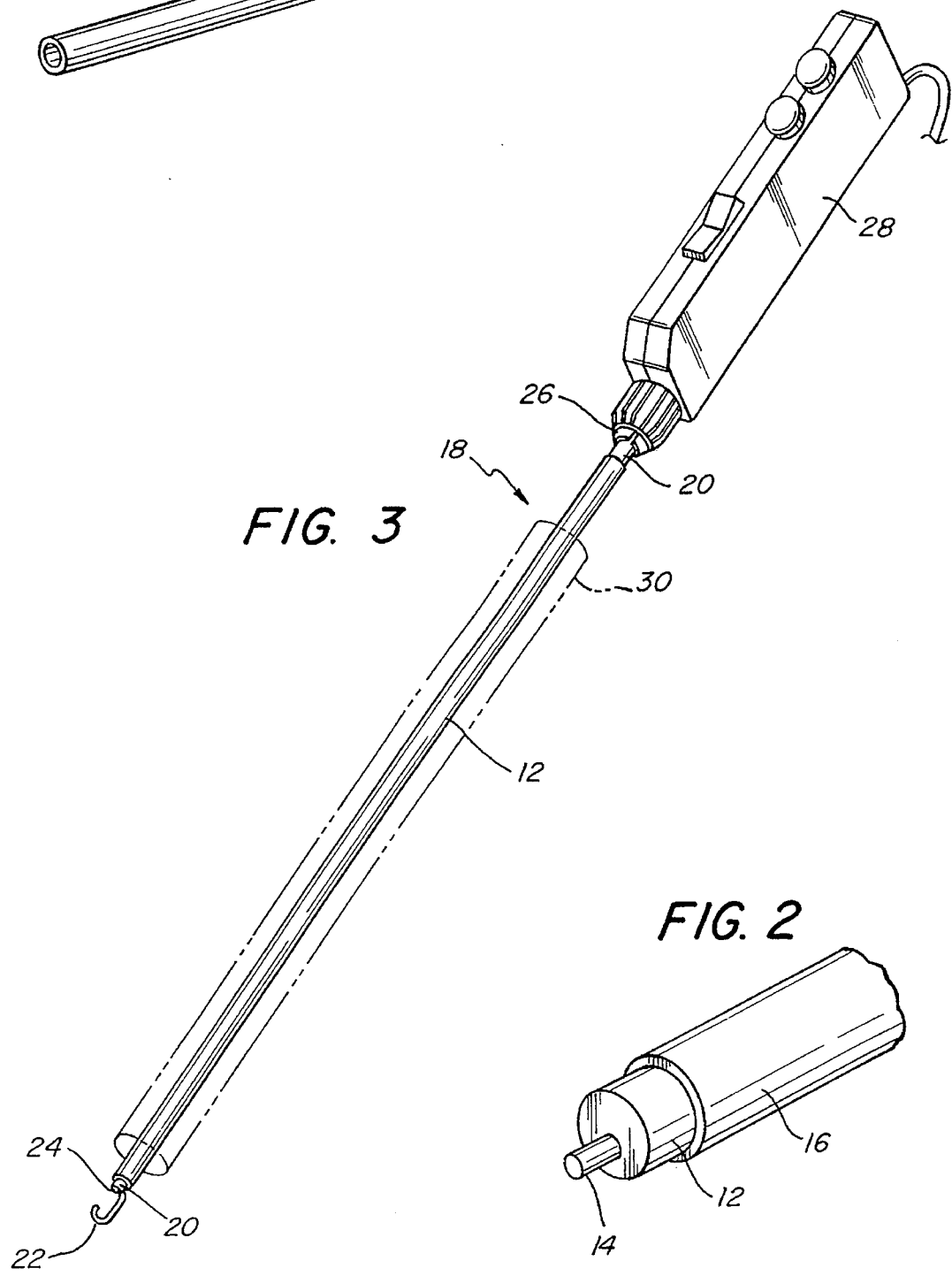
FIG. 3 is a perspective view of a electro-surgical instrument including an electrically conducting member and the subject polymeric tubing disposed thereon.

With reference to FIG. 3, an electrosurgical instrument is generally shown at 18. The instrument includes a generally cylindrical shaped electrically conducting member 20 equipped with a surgical attachment 22 secured to one end 24. The surgical attachment 22 may be of various types for performing a variety of surgical procedures. The opposite end 26 of the conducting member 20 is secured to a hand-held control module 28 which provides electrical current, vacuum pressure, fluid pressure, etc, through the conducting member 20, to the surgical attachment 22; thus, permitting a surgeon to control the surgical attachment 22, e.g. for irrigating, providing suction, coagulating vessels, etc.

The conducting member 20 includes the subject tubing 12 disposed circumferencally about its length. The tubing 12 is formed so as to have a inner diameter larger than the outer diameter of the conducting member 20 thereby permitting the tubing 12 to be disposed over the conducting member 20. The tubing 12 is subsequently heat shrunk into a fluid tight adhesive seal about the conducting member 20. This fluid tight seal holds up after cyclic autoclave, gamma, electron beam, and ethylene oxide gas sterilization. Not only does the tubing 10 provide a fluid tight seal, it simultaneously maintains a sufficient hot modulus and electric insulative properties after cyclic sterilization.

The tubing 12 is preferably transparent thereby permitting one to view the conducting member 20 disposed within the tubing 12. Moreover, the tubing 12 does not permanently dis-color after cyclic gamma, electron beam, or ethylene oxide gas sterilization.

The instrument may optionally include a second tubing 30 disposed about the polymeric tubing 12, as shown in phantom in FIG. 3. The second tubing 30 is adhesively bonded to the polymeric tubing 12 in the same manner as polymeric tubing 16 as previously described above with reference to FIG. 2. The second tubing 30 remains adhesively sealed to the conducting member 20 by the polymeric tubing 12,. even after cyclic autoclave sterilization.

The invention has been described in an illustrative manner, an it is to be understood the terminology used is intended to be in the nature of description rather than of limitation.

Obviously many modification and variation of the present invention are possible in light of the above teachings. Therefor, it is to be understood that within the scope of the appended claims, wherein reference numerals are merely for convenience and are not to be in any way limiting, the invention may be practiced otherwise than as specifically described.

I claim:

1. A tubing consisting essentially of a crosslinked acrylated polyolefin, having been sterilized, and being adhesive to a substrate and heat sealable after cyclic autoclave sterilization and being resistant to permanent discolorization after cyclic gamma and electron beam sterilization.

2. A tubing as set forth in claim 1 further characterized by said acrylated polyolefin consisting essentially of a copolymer of ethylene and methacrylic acid.

3. A tubing as set forth in claim 2, further characterized by said acrylated polyolefin having a melt index range from 1.5 to 500.

4. A tubing as set forth in claim 3 further characterized by said acrylated polyolefin having an acid number from 4 to 90.

5. A tubing as set forth in claim 4 further characterized by consisting essentially of a branched, random ethylene methacrylic acid copolymer having carboxyl groups distributed along the polymer chain.

6. A tubing as set forth in claim 2 further characterized by being heat shrinkable.

\* \* \* \* \*